US010055541B2

(12) United States Patent
Werner

(10) Patent No.: US 10,055,541 B2
(45) Date of Patent: Aug. 21, 2018

(54) VISUALIZATION AND NAVIGATION OF KNOWLEDGE DOMAINS

(71) Applicant: Horst Werner, Muehlhausen-Rettigheim (DE)

(72) Inventor: Horst Werner, Muehlhausen-Rettigheim (DE)

(73) Assignee: SAP SE, Walldorf (DE)

( * ) Notice: Subject to any disclaimer, the term of this patent is extended or adjusted under 35 U.S.C. 154(b) by 966 days.

(21) Appl. No.: 14/528,081

(22) Filed: Oct. 30, 2014

(65) Prior Publication Data

US 2015/0058771 A1     Feb. 26, 2015

Related U.S. Application Data

(63) Continuation-in-part of application No. 13/650,855, filed on Oct. 12, 2012, now abandoned.

(51) Int. Cl.
*G06F 19/26* (2011.01)
*G06F 3/0481* (2013.01)
(Continued)

(52) U.S. Cl.
CPC ............ *G06F 19/26* (2013.01); *G06F 3/0481* (2013.01); *G06F 17/30554* (2013.01);
(Continued)

(58) Field of Classification Search
CPC .......... G06F 19/26; G06F 19/30; G06F 19/70; G06F 19/24; G06F 19/322; G06F 3/0481;
(Continued)

(56) References Cited

U.S. PATENT DOCUMENTS 5,619,632 A * 4/1997 Lamping ............... G06T 11/206
345/441
5,835,085 A * 11/1998 Eick .................... H04M 3/2254
715/853
(Continued)

OTHER PUBLICATIONS

Fairchild, K. M., Poltrock, S.E., and Furnas, G.W., "SemNet: three-dimensional graphic representations of large knowledge bases," Cognitive Science and its Applications for Human Computer Interaction, Lawrence Erlbaum, Hillsdale, N.J., 1988, Editor: Guindon, R., pp. 201-233.*

(Continued)

*Primary Examiner* — Yongjia Pan
*Assistant Examiner* — Maria S Ayad
(74) *Attorney, Agent, or Firm* — Schwegman Lundberg & Woessner, P.A.

(57) ABSTRACT

A system stores visual content, and displays the visual content on a display unit in an undistorted, overview projection. The system receives input from a user to focus on a topic in the undistorted, overview projection, and transforms the undistorted, overview projection into a focused display showing the topic selected by the user and content related to the topic selected by the user in a continuous sequence of increasingly distorted projections. In the focused display, the content that is not related to the topic selected by the user does not move on the focused display, and the content that is related to the topic selected by the user moves towards the topic selected by the user on the focused display.

2 Claims, 7 Drawing Sheets

(51) Int. Cl.
  *G06F 17/30* (2006.01)
  *G06F 19/24* (2011.01)
  *G06T 19/20* (2011.01)
(52) U.S. Cl.
  CPC .. *G06F 17/30696* (2013.01); *G06F 17/30713* (2013.01); *G06F 17/30864* (2013.01); *G06F 17/30994* (2013.01); *G06F 19/24* (2013.01); *G06F 2203/04805* (2013.01); *G06T 19/20* (2013.01)
(58) Field of Classification Search
  CPC . G06F 2203/04804; G06F 2203/04805; G06F 2203/04806; G06F 17/30994; G06F 17/30696; G06F 17/3084; G06F 17/30713; G06F 17/30554; G06F 17/30864; G06Q 30/0643; G06Q 10/02; G06Q 10/0633; G06Q 20/10; G06Q 20/322; G06Q 20/38; G06Q 30/0222; G06Q 30/0257; G06Q 30/0261; G06Q 40/06; G06Q 40/08; G06Q 40/12; G06Q 50/26; G06T 11/206; G06T 19/20; G06T 5/002; G06T 7/0012; G06T 7/0016
  See application file for complete search history.

(56) References Cited

U.S. PATENT DOCUMENTS

| | | | | |
|---|---|---|---|---|
| 6,237,006 | B1* | 5/2001 | Weinberg | G06F 11/32 345/419 |
| 6,377,287 | B1* | 4/2002 | Hao | G06F 17/30994 707/E17.142 |
| 6,470,383 | B1* | 10/2002 | Leshem | G06F 11/32 707/E17.116 |
| 6,868,525 | B1* | 3/2005 | Szabo | G06F 17/30067 705/14.53 |
| 6,897,885 | B1* | 5/2005 | Hao | G06F 17/30905 707/E17.011 |
| 7,143,392 | B2* | 11/2006 | Ii | G06F 11/323 717/125 |
| 7,549,309 | B2 | 6/2009 | Beringer | |
| 2002/0163517 | A1* | 11/2002 | Loomis | G06T 11/206 345/440 |
| 2003/0007002 | A1* | 1/2003 | Hida | G06T 11/206 715/734 |
| 2003/0067498 | A1* | 4/2003 | Parisi | G06F 17/2735 715/853 |
| 2004/0030741 | A1* | 2/2004 | Wolton | G06F 17/30873 709/202 |
| 2006/0074926 | A1* | 4/2006 | Yakowenko | G06T 11/206 |
| 2007/0174872 | A1* | 7/2007 | Jing | G06F 17/30244 725/46 |
| 2007/0209025 | A1* | 9/2007 | Jing | G06F 17/30265 |
| 2007/0211056 | A1* | 9/2007 | Chakraborty | G06T 11/206 345/440 |
| 2008/0077875 | A1* | 3/2008 | Li | G06T 11/206 715/764 |
| 2010/0251153 | A1* | 9/2010 | Sangiovanni | G06F 3/04817 715/767 |
| 2014/0108980 | A1 | 4/2014 | Werner | |

OTHER PUBLICATIONS

Sarkar, M., & Brown, M. H. (Jun. 1992). Graphical fisheye views of graphs. In Proceedings of the SIGCHI conference on Human factors in computing systems (pp. 83-91). ACM.*
Bartram, Lyn, et al. "The continuous zoom: A constrained fisheye technique for viewing and navigating large information spaces." Proceedings of the 8th annual ACM symposium on User interface and software technology. ACM, 1995.*
Janecek, Paul, and Pearl Pu. "A framework for designing fisheye views to support multiple semantic contexts." Proceedings of the Working Conference on Advanced Visual Interfaces. ACM, 2002.*
Kreuseler, Matthias, and Heidrun Schumann. "A flexible approach for visual data mining." IEEE Transactions on Visualization and Computer Graphics 8.1 (2002): 39-51.*
"U.S. Appl. No. 13/650,855, Final Office Action dated Jul. 30, 2014", 22 pgs.
"U.S. Appl. No. 13/650,855, Non Final Office Action dated Apr. 24, 2014", 20 pgs.
"U.S. Appl. No. 13/650,855, Response filed Jun. 20, 2014", 9 pgs.
Fairchild, K M, et al., "SemNet: three-dimensional graphic representations of large knowledge base", Cognitive Science and its Applications for Human Computer Interaction, Lawrence Erlbaum, Hillsdale, (1998), 201-233.
Furnas, G. W, "Generalized fisheye views", Proceedings of the SIGCHI Conference on Human Factors in Computing Systems (CHI '86), (1986), 16-23.
Werner, H., et al., "Symbik—A New Medium for Collaborative Knowledge-Intensive Work", Proceedings of the International Conference on Education, Informatics and Cybernetics, (Orlando, Florida, Nov. 29-Dec. 2, 2011). icEIC 2011. IIIS, Winter Garden, Florida, (2011), 6 pgs.

* cited by examiner

VISUALIZATION AND NAVIGATION OF KNOWLEDGE DOMAINS

CROSS REFERENCE TO RELATED APPLICATION

The present application is a continuation-in-part and claims priority benefit from U.S. patent application Ser. No. 13/650,855 filed on Oct. 12, 2012, and entitled "VISUALIZATION AND NAVIGATION OF KNOWLEDGE DOMAINS," which is incorporated herein by reference.

TECHNICAL FIELD

The present disclosure relates to visualization and navigation of knowledge domains, and in an embodiment, but not by way of limitation, a system and method to visualize and interactively navigate complex knowledge domains.

BACKGROUND

Visual and/or tangible representations are a particularly efficient means of conveying knowledge. However, conventional visualizations can only cover a limited complexity. Consequently, complex content must be split up into multiple visual representations representing different topics or different views on one topic. The most common way to present such visualizations is a slideshow, which contains the different views in a sequential form. A drawback of such slideshow sequences is that they can't properly convey the network structure inherent to all complex knowledge domains. Additionally, it is difficult to build a comprehensive mental picture from sequences of many limited and rather disconnected representations. Several other interactive visualization/navigation techniques (including hyperlinks, navigation graphs, trees, zoomable, and/or distorted representations) have been developed in the art. However, due to geometrical constraints—none of these techniques provides a seamless integration of a comprehensive overview with detailed focused views that express the relatedness of topics by geometric proximity.

DETAILED DESCRIPTION

Figure 1A:
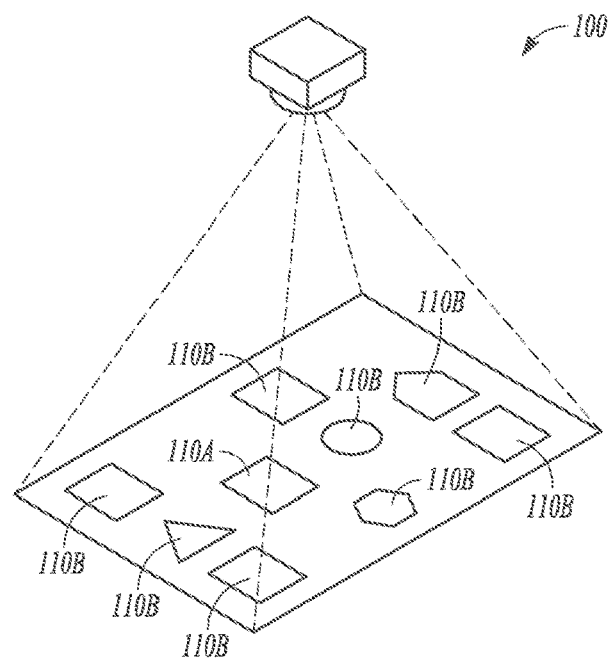
FIG. 1A is an example of an undistorted overview of visual content.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

As noted in the background section, visual and/or tangible representations are a particularly efficient means of conveying knowledge. However, conventional visualizations can only cover a limited complexity. Consequently, complex content must be split up into multiple visual representations representing different topics or different views on one topic.

The most common way to present such visualizations is a slideshow, which contains the different views in a sequential form. A drawback of such slideshow sequences is that the sequences can't properly convey the network structure inherent to all complex knowledge domains. An additional drawback is that it is difficult to build a comprehensive mental picture from sequences of many limited and rather disconnected representations.

Consequently, a number of more interactive presentation forms have been developed that allow a user to navigate a network structure of interrelated topics. For example, one solution is a connection of visualizations by means of hyperlinks. However, the hard context changes (i.e., switching of window content) invoked by following a hyperlink make it hard for a user to follow and maintain the overall picture. That is, users tend to get lost in what they perceive as a labyrinth of interrelated information.

Many different implementations of (dynamically created) navigation graphs have been used, but in cases with large numbers of strongly interconnected topic nodes the sheer amount of interconnections makes it difficult to interpret and absorb the conveyed information. Notwithstanding, there are two adaptations.

First, an adaptation can display only a very limited range of the graph around a center node, which changes at every navigation step. This approach has the disadvantage that no comprehensive view ("big picture") is provided. However, an extension of this concept, such as displaying common properties of multiple directly associated nodes and the selective addition of indirectly associated nodes (as described in U.S. Pat. No. 7,549,309) can mitigate this disadvantage to a certain degree.

Second, an adaptation can display only strictly hierarchical graphs (i.e., tree structures), which solves the problem of having too many crossing lines, but it negates the networked structure of the knowledge domain. A specific variant of this approach is the projection of such a tree on a hyperbolic surface which allows to display the (few) nodes close to the center in detail, and yet show a rather big range of the graph since size and distances are increasingly downscaled with increasing distance to the center.

A projection on a hyperbolic surface is a specific implementation of a fisheye view. Fisheye user interfaces are a well-understood means of providing at the same time a high level of detail for areas of interest and global context with low level of detail. While they are useful in certain cases where both detail and context information are needed, a high degree of distortion has been reported as detrimental to user orientation.

Another increasingly popular approach for the visual representation of complex knowledge domains is realized in zoomable user interfaces. The ability to lay out visualizations on a virtually infinite plane and zoom into certain regions to display them in varying level of detail is a very intuitive and powerful way to convey information simultaneously as "big picture" and in very fine-grained details. The relatedness of topics can approximately be represented by their spatial distance in such a layout. However, for a sufficiently large amount of highly interrelated topics, there exists no arrangement wherein the distance from each topic to each related topic is small enough to convey the relatedness. One prior art system mitigates this problem by allowing the definition of a "path" that the (virtual) camera takes during a presentation, and which can connect rather distant regions by one "navigation step". However, such a path is a one-dimensional sequence which is in principle the same thing as the sequence of slides in a conventional presentation.

Another prior art system approaches this problem by allowing the creation of several graphical representations of the same topic on an infinite, zoomable layout area, and providing an automatic way to move the virtual camera from one occurrence to the next in a chain. A disadvantage of this approach is that the navigation affordance and the context of the navigation target are not obvious.

Consequently, what is missing from the prior art is a way of visually representing complex interrelated knowledge domains in such a way that a user can seamlessly move from a comprehensive big picture to very detailed views of specific topics, see graphical representations of all related topics while inspecting a specific topic, and navigate to the detailed views of the related topics without a context break, i.e., by continuously moving through the "big picture."

To address these shortcomings in the prior art, an embodiment includes a computer processor which controls a user interface. The user interface displays visual content in a fully zoomable undistorted (i.e., angle-preserving) projection in an overview mode, and also allows a seamless transition into a distorted (e.g., hyperbolic) projection when a user focuses on a specific topic. In the course of this transition, the plane on which the content is projected gradually cambers into a hyperboloid, a paraboloid, or other projection. Simultaneously, an underlying representation of the relatedness between the visualized topics is evaluated. The content that is not related to the focus topic remains in the cambering plane and finally fades out (i.e., becomes invisible or disappears) of the user interface display during the transition, independent of its geometric proximity to the focus topic on the user interface display. The related content objects move independently toward the focus object on the user interface display. In a resulting fisheye view, the downscaled visualizations of the related topics act as visual hyperlinks. Clicking on one of these visualizations invokes a virtual camera movement towards the clicked topic. During this movement, the fisheye effect is temporarily decreased, i.e. the distortion of the plane is reduced and unrelated topics become visible with a certain transparency value. At the end of the movement, the user interface is refocused, as a fisheye view again, on the new topic. The user can switch back from fisheye view to the undistorted view at any time, e.g., by clicking on the background of the plane. The transition back to the undistorted view is performed exactly like the focusing transition, only in a reverse sequence. In an embodiment, the animation paths of the objects related to the focus topic are calculated in a manner such that, in the very beginning of the transformation, their movement obeys the cambering hyperboloid projection, and in the course of the transformation their paths are increasingly decoupled from the projected plane as detailed in the formulae below.

An embodiment provides a completely continuous way of exploring complex interrelated content. That is, a spatially coherent overview provides orientation, and the fisheye view visually conveys the semantic proximity of interrelated topics that cannot be visualized in the Euclidian geometry of the undistorted plane. An improvement of this embodiment is the seamless transition between the two visualizations that avoids disorientation of the user. In other words, the embodiment provides a new kind of visual hyperlink with the advantages of conventional hyperlinks, that is, the ability to navigate arbitrary network structures, without the disadvantage of conventional hyperlinks, that is, the lack of "preview" of the navigation target and the hard context change (between screen shots).

Figure 1B:
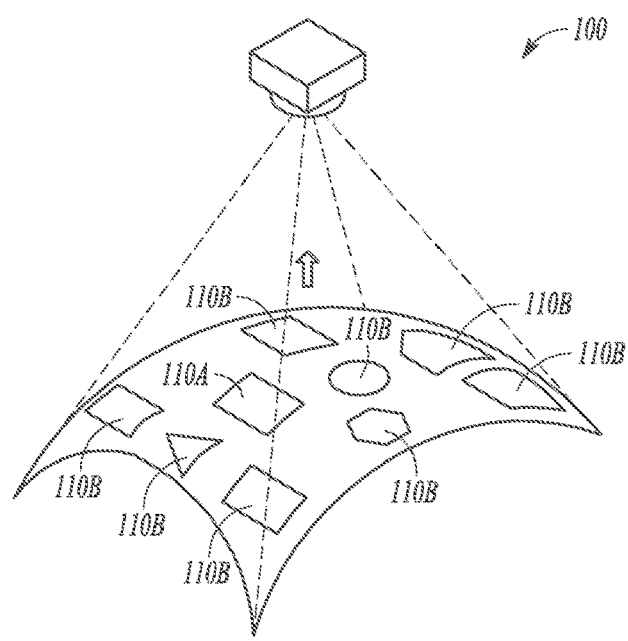
FIG. 1B is an example of a fisheye view of the visual content of FIG. 1A.

As noted, an embodiment is a user interface that displays visual content in a fully zoomable undistorted (i.e., angle-preserving) projection in an overview mode, and also allows the seamless transition into a distorted (e.g., hyperbolic) projection when the user focuses on a specific topic. FIG. 1A illustrates an undistorted display 100, which includes several pieces of visual content 110A and 110B. FIG. 1B illustrates an example of a distorted or hyperbolic projection, wherein one of the pieces of visual content 110A is focused upon and other pieces of visual content 110B are deemphasized in the fisheye view. As illustrated in FIGS. 1A and 1B, in the course of this transition, the plane on which the content is projected gradually cambers into a hyperboloid. Simultaneously, an underlying representation of the relatedness between the visualized topics is evaluated and all content that is not related to the focus topic fades out during the transition.

Figure 2A:
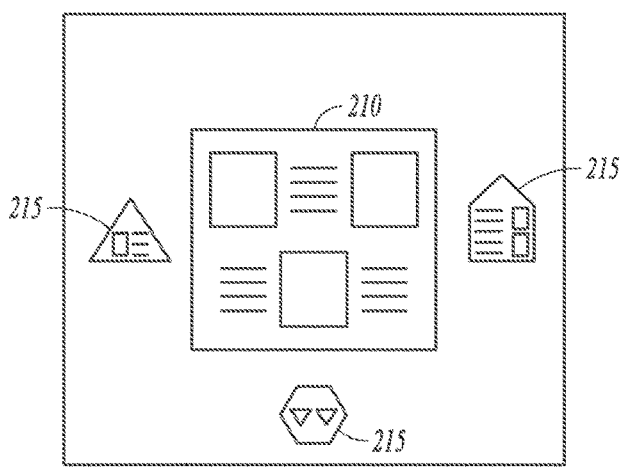
FIGS. 2A, 2B, and 2C illustrate movement through visual content.
Figure 2B:
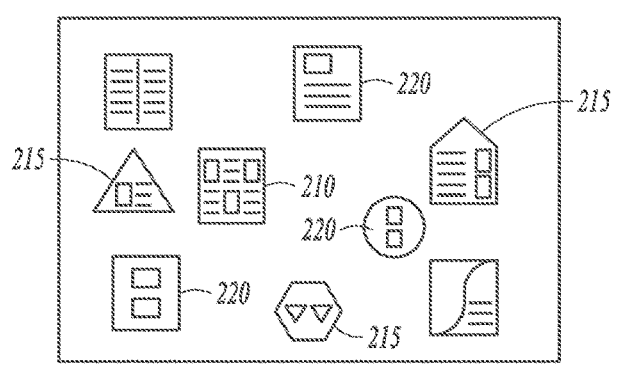
Figure 2C:
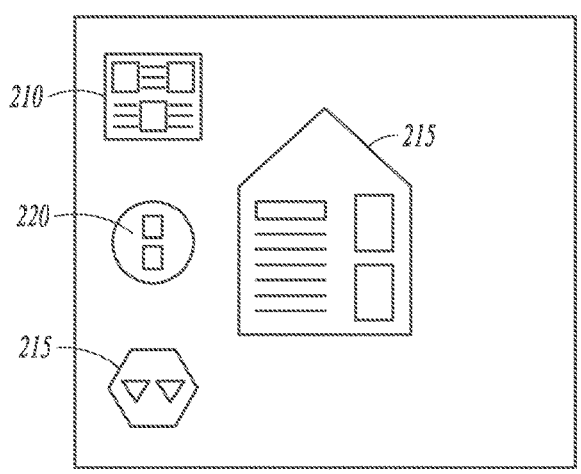

In the resulting fisheye view (FIG. 2A), the downscaled visualizations of the related topics act as visual hyperlinks. Clicking on one of these visualizations invokes a virtual camera movement towards the clicked topic, as is illustrated in FIGS. 2A, 2B, and 2C. During this movement the fisheye effect is temporarily decreased, i.e. the distortion of the plane is reduced and unrelated topics become visible with a certain transparency value. At the end of the movement, the user interface is refocused, as a fisheye view again, on the new topic. Specifically, as illustrated in FIG. 2A, a user can select visual content or hyperlink 215, which is displayed with the selected visual content 210. As noted, the view in FIG. 2A, if no other links are further selected, will transform back from the fisheye projection to an undistorted view and then will immediately transform again into a fisheye view as displayed in FIG. 2C, focused on the visual content 215 that the user clicked. As can be seen in FIG. 2C, the related content for that link is also displayed. The related content for a link 215 may be the same as the related content for the link 210 in FIG. 2A, or it may be different. In FIG. 2C, the related content is different than the related content in FIG. 2A. Specifically, the related content of FIG. 2C includes the visual content 210, one of the pieces of visual content 215 from FIG. 2A, and a new piece of related content 220. The user can switch back from fisheye view to the undistorted view (FIG. 2B) at any time, e.g., by clicking on the background of the plane. The transition back to the undistorted view is performed exactly like the focusing transition in reverse sequence, which is explained in further detail below.

An embodiment uses an algorithm that allows a seamless and gradual transition from a linear projection to a fisheye (e.g., hyperbolic) projection. During this transition, the algorithm treats objects that are unrelated to the focus object and related objects in a different way. That is, the unrelated objects strictly obey the rules of the fisheye projection and fade out. The related objects however remain visible, and at the end of the transition, the position and size of the related objects relative to the focus object have specific values to ensure good visibility of the related objects.

An implementation uses a hyperbolic projection to transform the logical coordinates into projected coordinates (pixel positions on the screen) and functions as follows. The coordinates of all objects are transformed into polar coordinates relative to the focus object for calculating the fisheye projection. The angle remains unchanged, but the size and distance of the related object relative to the focus object are changed as follows by the projection.

First, the following are defined:
f—a factor indicating the degree of the fisheye distortion.
d—the logical (undistorted) distance of an object to the center of the focus object.
r—the projected distance of an object to the center of the focus object.
h—the logical horizon, i.e., the logical distance between the center of the focus object and the center of an object at the border of the screen.
$r_h$—the projected horizon, i.e., the number of pixels from the center of the screen to the border of the screen.

As noted above, in this implementation, the projection is hyperbolic. Hyperbolic means that the projected distance from the center for objects in infinite (logical) distance converges to a given projected radius, referred to as $r_\infty$. The formula for calculating the projected distance then is:

$$r(d) = r_\infty \left(1 - \frac{1}{fd+1}\right)$$

The convergence radius $r_\infty$ is calculated from $r_h$, h and f:

$$r_\infty = \frac{r_h}{1 - \frac{1}{fh+1}}$$

The scale factor at a point with the logical distance d from the center can be calculated from these formulas as the ratio r(d)/d:

$$\frac{r(d)}{d} = \frac{r_h}{h}\left(\frac{fh+1}{fd+1}\right)$$

For an undistorted linear projection, the scale factor has a constant value of $$\frac{r_h}{h}.$$

It can be seen that for sufficiently small values of f, the factor $$\frac{f\ h+1}{f\ d+1}$$

gets close to 1, which means that a seamless transition from an undistorted view to the fisheye projection can be achieved by starting with a very small value of f, for example 0.0001, and gradually increasing it, for example up to 0.005. In order to create a seamless transition of the projection of the related objects from a strict projection towards a predetermined projected distance (e.g., 70% of the horizon) and size, the following method can be used.

After calculating the logical distance d, but before calculating the projected distance, the logical distance is adjusted according to the current stage of the animation, and the projected distance and size are calculated on the basis of the adjusted logical distance. Now, the following are defined:
d'—the adjusted logical distance.
$d_{target}$—the adjusted logical distance at the end of the animation, e.g., 0.7 h.
$f_1$—the fisheye factor at the end of the animation.
$f_0$—the fisheye factor at the start of the animation.
f—the fisheye factor at the current animation step.
Then.

$$d' = \frac{d_{target} - d}{f_1 - f_0}(f - f_0) + d$$

Figure 3A:
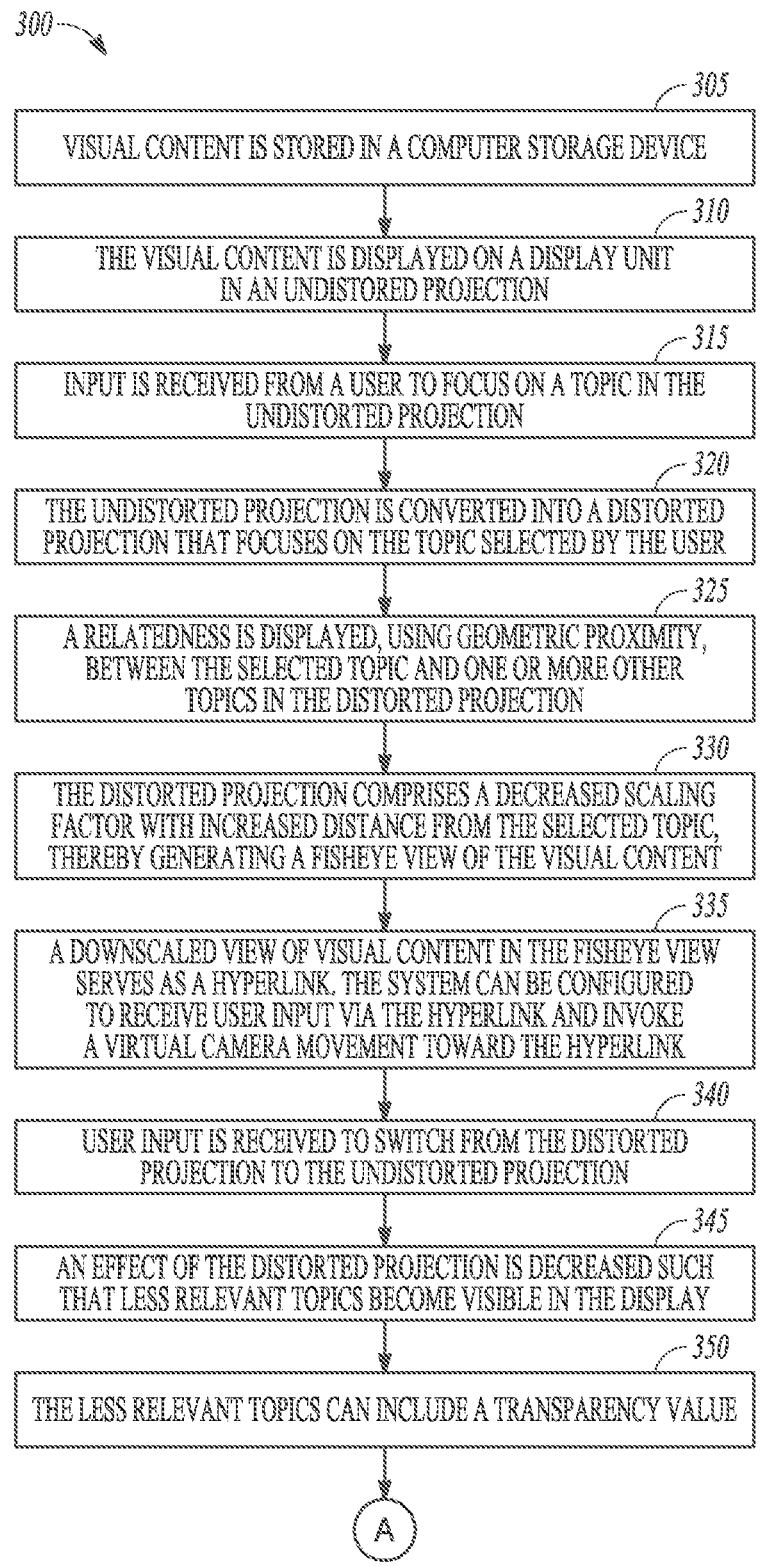
FIGS. 3A and 3B are a flowchart-like diagram illustrating steps and features of a system and method that permits a user to alternate between an undistorted overview of visual content and a fisheye view of the visual content.
Figure 3B:
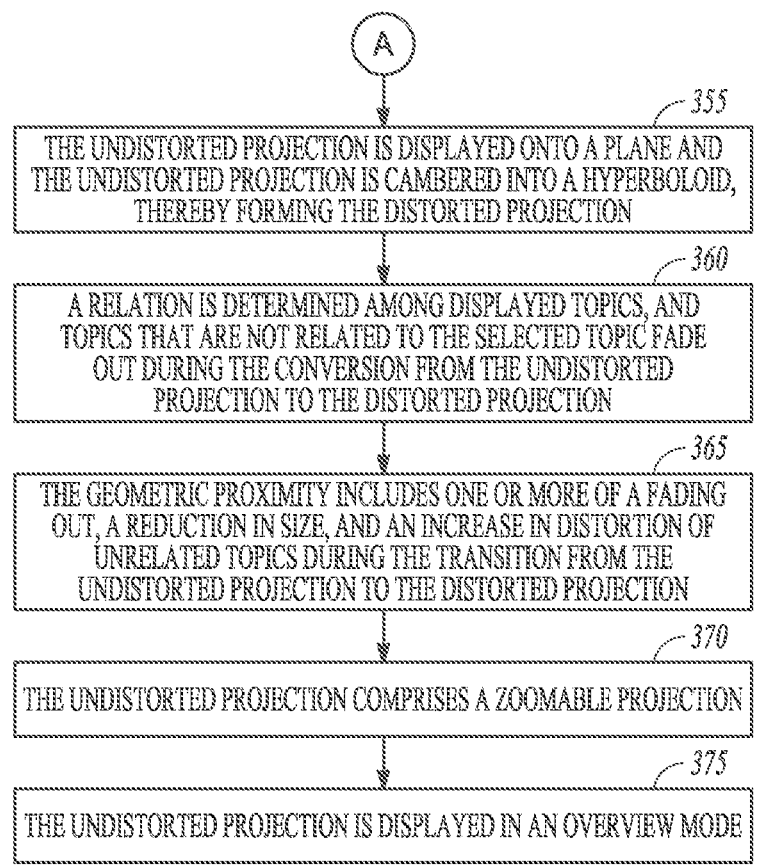

FIGS. 3A and 3B are a flowchart-like diagram of features and steps of an example process 300 for transitioning between views of visual content. FIGS. 3A and 3B include a number of process blocks 305-375. Though arranged serially in the example of FIGS. 3A and 3B, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

At 305, visual content is stored in a computer storage device. At 310, the visual content is displayed on a display unit in an undistorted projection. At 315, input is received from a user to focus on a topic in the undistorted projection. At 320, the undistorted projection is converted into a distorted projection that focuses on the topic selected by the user. At 325, a relatedness is displayed, using geometric proximity, between the selected topic and one or more other topics in the distorted projection. The geometric proximity can include such factors as the size of a particular piece of visual content, the distance between two pieces of visual content, and overlap of two pieces of visual content. The relatedness can be based on virtually anything that relates two of more topics, such as for example, the topics originate from the same division within a company, the topics both relate to sales of a company, and the topics both reflect data created in the same calendar year.

At 330, the distorted projection comprises a decreased scaling factor with increased distance from the selected topic, thereby generating a fisheye view of the visual content. At 335, a downscaled view of visual content in the fisheye view serves as a hyperlink. The downscaled view results in one or more of moving a topic to the background of the display, making the topic smaller, making the topic translucent, and accentuating the hyperbolic features of the topic. Also at 335, the system can be configured to receive user input via the hyperlink and invoke a virtual camera movement toward the hyperlink.

At 340, user input is received to switch from the distorted projection to the undistorted projection. The received user input can be a clicking on a background of the distorted projection. At 345, an effect of the distorted projection is decreased such that less relevant topics become visible in the display. At 350, the less relevant topics can include a transparency value. The transparency value will determine the translucent nature of the topic's visual content display, wherein for example, a higher value translates into a more translucent visual topic.

At 355, the undistorted projection is displayed onto a plane and the undistorted projection is cambered into a hyperboloid, thereby forming the distorted projection. In other embodiments, a parabola or other projection could be used in lieu of a hyperbola.

At 360, a relation is determined among displayed topics, and topics that are not related to the selected topic fade out during the conversion from the undistorted projection to the distorted projection. The relation between topics can be determined many ways. For example, it could be manually oriented wherein a user identifies the topics that he or she would like to be treated as related. In another example, the determination of the relatedness of the topics could be more automatic, such as configuring a computer processor to search for and match key words from among several topics.

At 365, the geometric proximity includes one or more of a fading out, a reduction in size, and increase or decrease in distance between pieces of visual content, and an increase in distortion of unrelated topics during the transition from the undistorted projection to the distorted projection. At 370, the undistorted projection comprises a zoomable projection. And at 375, the undistorted projection is displayed in an overview mode.

Figure 4A:
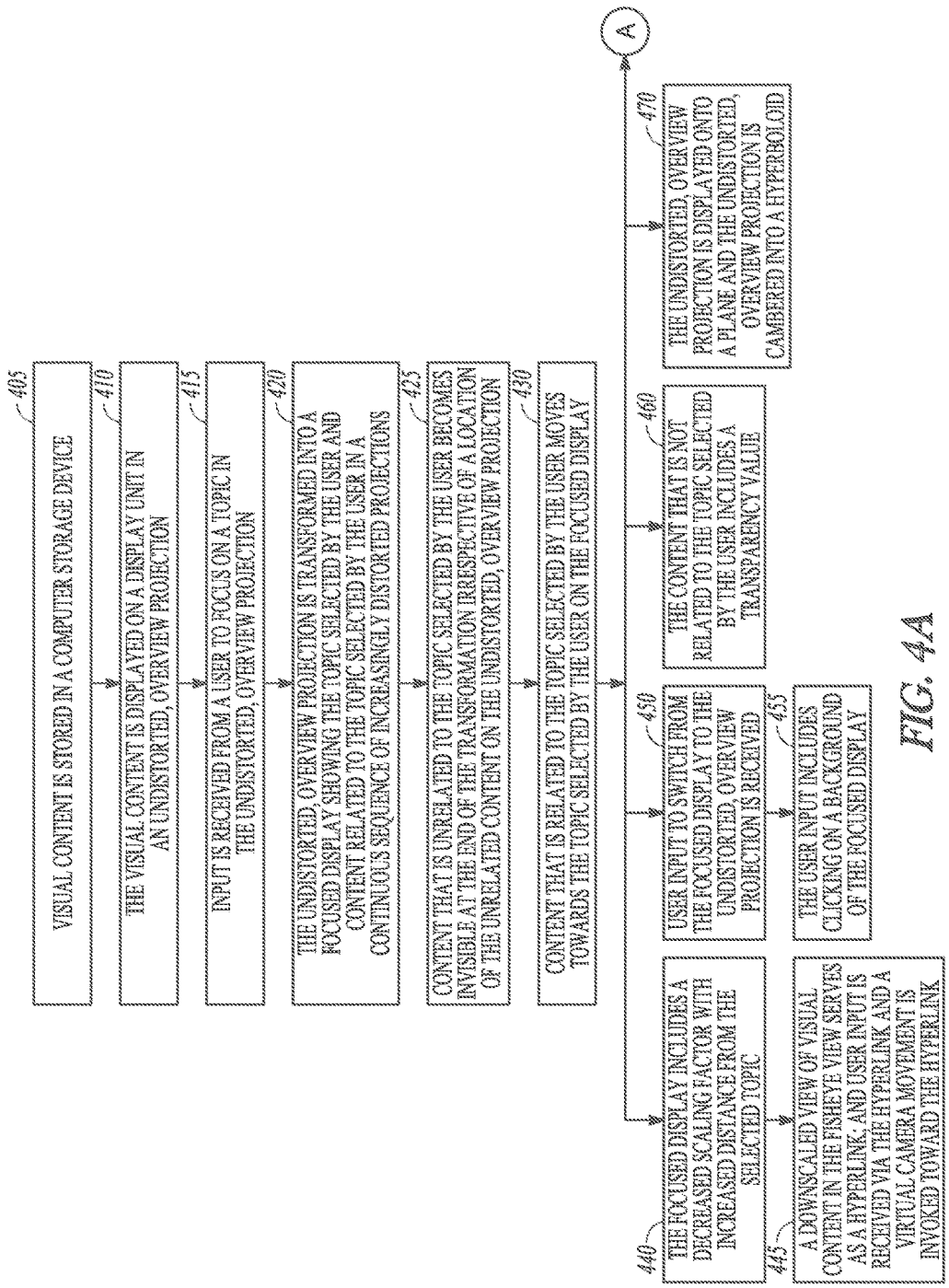
FIGS. 4A and 4B are a flowchart-like diagram illustrating steps and features of another system and method that permits a user to alternate between an undistorted overview of visual content and a fisheye view of the visual content.
Figure 4B:
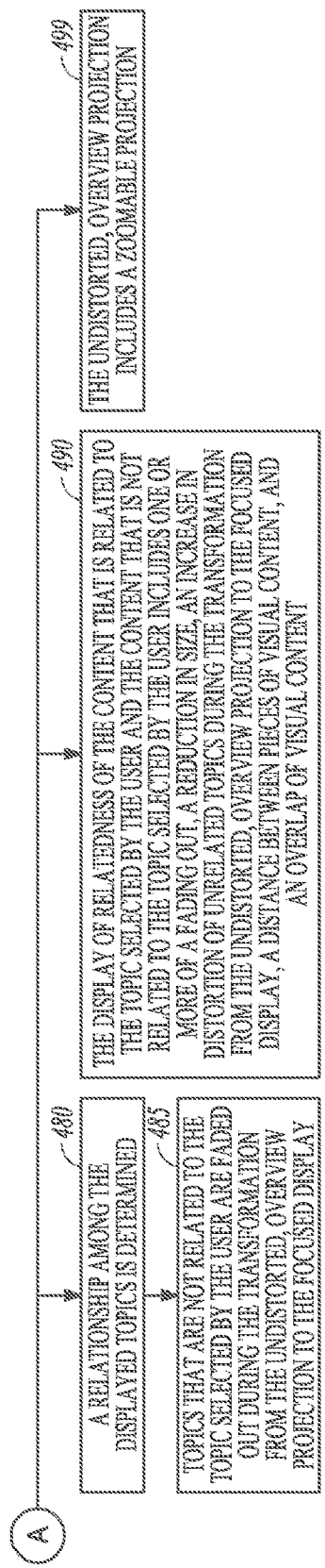

FIGS. 4A and 4B are a flowchart-like diagram of features and steps of another example process 400 for transitioning between views of visual content. FIGS. 4A and 4B include a number of process blocks 405-499. Though arranged serially in the example of FIGS. 4A and 4B, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

At 405, visual content is stored in a computer storage device. At 410, the visual content is displayed on a display unit in an undistorted, overview projection. At 415, input is received from a user to focus on a topic in the undistorted, overview projection. At 420, the undistorted, overview projection is transformed into a focused display showing the topic selected by the user and content related to the topic selected by the user in a continuous sequence of increasingly distorted projections. At 425, content that is unrelated to the topic selected by the user becomes invisible at the end of the transformation irrespective of a location of the unrelated content on the undistorted, overview projection. At 430, content that is related to the topic selected by the user moves towards the topic selected by the user on the focused display.

In an embodiment, operation 425 addresses a particular issue. That is, related content and unrelated content can be initially geometrically close to the selected topic or geometrically distant from the selected topic, which can be the result of the graph layout. Consequently, operation 425 covers the situation wherein the unrelated content is both near the selected topic and distant from the selected topic. Irrespectively, the unrelated content becomes invisible at the end of the transformation, even if the unrelated content was near the selected topic and its movement on the display device was not sufficient to remove the unrelated content from the field of view of the display device. Another way of stating this is that the invisibility of the unrelated content at the end of the transformation is independent of the location of the unrelated content on the undistorted, overview projection.

At 440, the focused display includes a decreased scaling factor with increased distance from the selected topic. This decreased scaling factor generates a fisheye view of the visual content. At 445, a downscaled view of visual content in the fisheye view serves as a hyperlink. Further at 445, user input is received via the hyperlink and a virtual camera movement is invoked toward the hyperlink.

At 450, user input to switch from the focused display to the undistorted, overview projection is received, and at 455, the user input includes clicking on a background of the focused display.

At 460, the content that is not related to the topic selected by the user includes a transparency value.

At 470, the undistorted, overview projection is displayed onto a plane and the undistorted, overview projection is cambered into a hyperboloid. This displaying and cambering forms the focused display.

At 480, a relationship among the displayed topics is determined. At 485, topics that are not related to the topic selected by the user are faded out during the transformation from the undistorted, overview projection to the focused display.

At 490, the display of relatedness of the content that is related to the topic selected by the user and the content that is not related to the topic selected by the user includes one or more of a fading out, a reduction in size, an increase in distortion of unrelated topics during the transformation from the undistorted, overview projection to the focused display, a distance between pieces of visual content, and an overlap of visual content.

At 499, the undistorted, overview projection includes a zoomable projection.

Example Embodiments

Example No. 1 is a system that includes a computer processor and a computer storage device that are configured to store visual content in the computer storage device; display the visual content on a display unit in an undistorted projection; receive input from a user to focus on a topic in the undistorted projection; convert the undistorted projection into a distorted projection that focuses on the topic selected by the user; and display a relatedness, using geometric proximity, between the selected topic and one or more other topics in the distorted projection.

Example No. 2 includes the features of Example No. 1, and optionally includes a system wherein the distorted projection comprises a decreased scaling factor with increased distance from the selected topic, thereby generating a fisheye view of the visual content.

Example No. 3 includes the features of Example Nos. 1-2, and optionally includes a system wherein a downscaled view of visual content in the fisheye view serves as a hyperlink, and wherein the computer processor is configured to receive user input via the hyperlink and invoke a virtual camera movement toward the hyperlink.

Example No. 4 includes the features of Example Nos. 1-3, and optionally includes a system wherein the computer processor is configured to receive user input to switch from the distorted projection to the undistorted projection.

Example No. 5 includes the features of Example Nos. 1-4, and optionally includes a system wherein the user input comprises clicking on a background of the distorted projection.

Example No. 6 includes the features of Example Nos. 1-5, and optionally includes a system wherein the computer processor is configured to decrease an effect of the distorted projection such that less relevant topics become visible in the display.

Example No. 7 includes the features of Example Nos. 1-6, and optionally includes a system wherein the less relevant topics comprise a transparency value.

Example No. 8 includes the features of Example Nos. 1-7, and optionally includes a system wherein the computer processor is configured to display the undistorted projection onto a plane and to camber the undistorted projection into a hyperboloid, thereby forming the distorted projection.

Example No. 9 includes the features of Example Nos. 1-8, and optionally includes a system wherein the computer processor is configured to determine a relation among displayed topics and fade out topics that are not related to the selected topic during the conversion from the undistorted projection to the distorted projection.

Example No. 10 includes the features of Example Nos. 1-9, and optionally includes a system wherein the geometric proximity comprises one or more of a fading out, a reduction in size, and an increase in distortion of unrelated topics during the transition from the undistorted projection to the distorted projection.

Example No. 11 includes the features of Example Nos. 1-10, and optionally includes a system wherein the undistorted projection comprises a zoomable projection.

Example No. 12 includes the features of Example Nos. 1-11, and optionally includes a system wherein the undistorted projection is displayed in an overview mode.

Example No. 13 is a process that includes the steps of storing visual content in the computer storage device, displaying the visual content on a display unit in an undistorted projection, receiving input from a user to focus on a topic in the undistorted projection, converting the undistorted projection into a distorted projection that focuses on the topic selected by the user, and displaying a relatedness, using geometric proximity, between the selected topic and one or more other topics in the distorted projection.

Example No. 14 includes the features of Example No. 13, and optionally includes a process wherein the distorted projection comprises a decreased scaling factor with increased distance from the selected topic, thereby generating a fisheye view of the visual content.

Example No. 15 includes the features of Example Nos. 13-14, and optionally includes a process wherein a downscaled view of visual content in the fisheye view serves as a hyperlink, and comprising receiving user input via the hyperlink and invoking a virtual camera movement toward the hyperlink.

Example No. 16 includes the features of Example Nos. 13-15, and optionally includes a process including receiving user input to switch from the distorted projection to the undistorted projection.

Example No. 17 is a computer readable storage device comprising instructions that when executed by a processor execute a process comprising storing visual content in the computer storage device; displaying the visual content on a display unit in an undistorted projection; receiving input from a user to focus on a topic in the undistorted projection; converting the undistorted projection into a distorted projection that focuses on the topic selected by the user; and displaying a relatedness, using geometric proximity, between the selected topic and one or more other topics in the distorted projection.

Example No. 18 includes the features of Example No. 17, and optionally includes a computer readable storage comprising instructions for decreasing an effect of the distorted projection such that less relevant topics become visible in the display; and wherein the less relevant topics comprise a transparency value.

Example No. 19 includes the features of Example Nos. 17-18, and optionally includes a computer readable storage device comprising instructions for determining a relation among displayed topics and fading out topics that are not related to the selected topic during the conversion from the undistorted projection to the distorted projection.

Example No. 20 includes the features of Example Nos. 17-19, and optionally includes a computer readable storage wherein the geometric proximity comprises one or more of a fading out, a reduction in size, and an increase in distortion of unrelated topics during the transition from the undistorted projection to the distorted projection.

Figure 5:
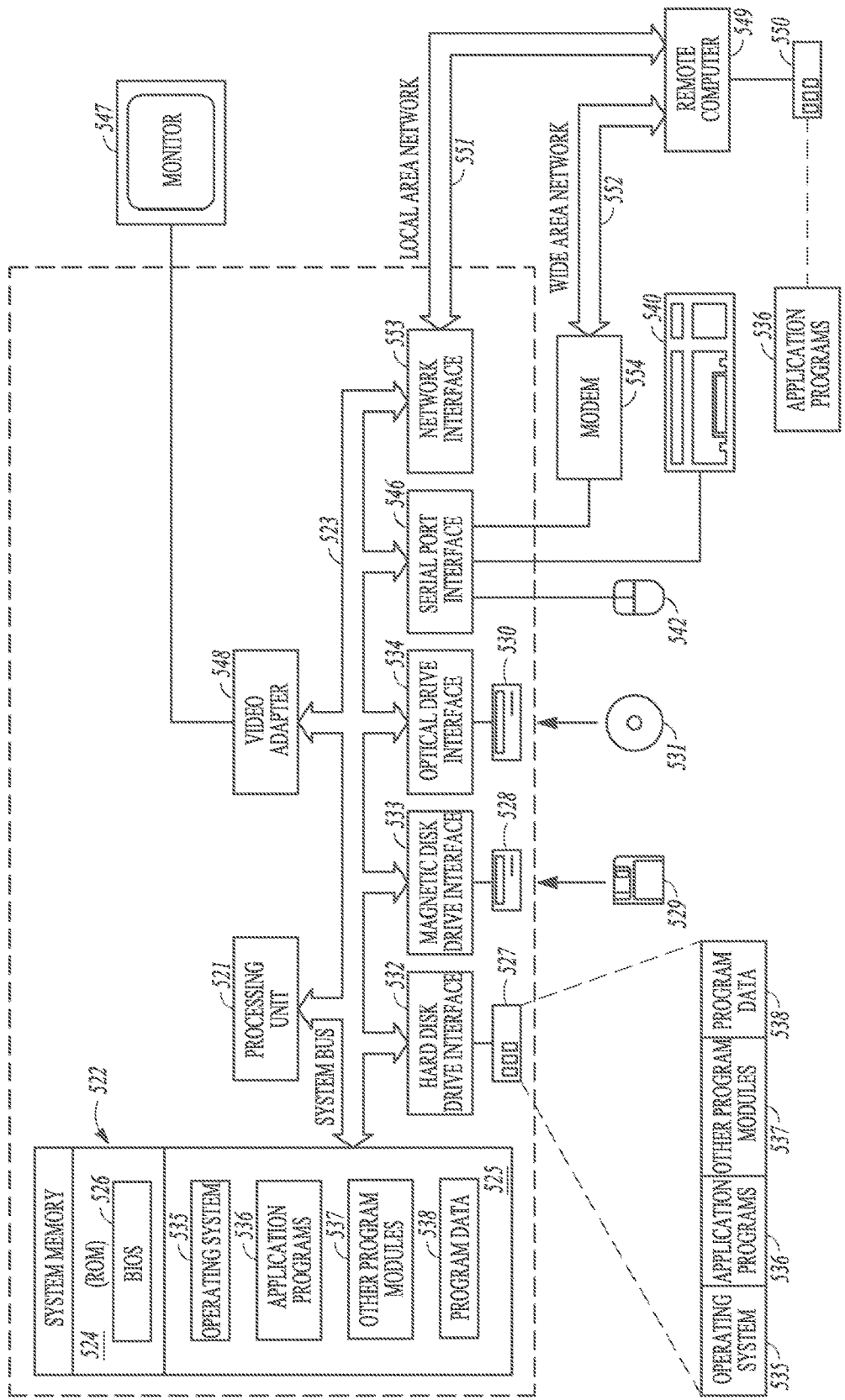
FIG. 5 is a block diagram of an example embodiment of a computer system upon which one or more embodiments of the present disclosure can execute.

FIG. 5 is an overview diagram of hardware and operating environment in conjunction with which embodiments of the invention may be practiced. The description of FIG. 5 is intended to provide a brief, general description of suitable computer hardware and a suitable computing environment in conjunction with which the invention may be implemented. In some embodiments, the invention is described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computer environments where tasks are performed by I/O remote processing devices that are linked through a communications network. In a distributed computing environment, program modules may be located in both local and remote memory storage devices.

In the embodiment shown in FIG. 5, a hardware and operating environment is provided that is applicable to any of the servers and/or remote clients shown in the other Figures.

As shown in FIG. 5, one embodiment of the hardware and operating environment includes a general purpose computing device in the form of a computer 20 (e.g., a personal computer, workstation, or server), including one or more processing units 21, a system memory 22, and a system bus 23 that operatively couples various system components including the system memory 22 to the processing unit 21. There may be only one or there may be more than one processing unit 21, such that the processor of computer 20 comprises a single central-processing unit (CPU), or a plurality of processing units, commonly referred to as a multiprocessor or parallel-processor environment. A multiprocessor system can include cloud computing environments. In various embodiments, computer 20 is a conventional computer, a distributed computer, or any other type of computer.

The system bus 23 can be any of several types of bus structures including a memory bus or memory controller, a peripheral bus, and a local bus using any of a variety of bus architectures. The system memory can also be referred to as simply the memory, and, in some embodiments, includes read-only memory (ROM) 24 and random-access memory (RAM) 25. A basic input/output system (BIOS) program 26, containing the basic routines that help to transfer information between elements within the computer 20, such as during start-up, may be stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 couple with a hard disk drive interface 32, a magnetic disk drive interface 33, and an optical disk drive interface 34, respectively. The drives and their associated computer-readable media provide non volatile storage of computer-readable instructions, data structures, program modules and other data for the computer 20. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, magnetic disk 29, optical disk 31, ROM 24, or RAM 25, including an operating system 35, one or more application programs 36, other program modules 37, and program data 38. A plug in containing a security transmission engine for the present invention can be resident on any one or number of these computer-readable media.

A user may enter commands and information into computer 20 through input devices such as a keyboard 40 and pointing device 42. Other input devices (not shown) can include a microphone, joystick, game pad, satellite dish, scanner, or the like. These other input devices are often connected to the processing unit 21 through a serial port interface 46 that is coupled to the system bus 23, but can be connected by other interfaces, such as a parallel port, game port, or a universal serial bus (USB). A monitor 47 or other type of display device can also be connected to the system bus 23 via an interface, such as a video adapter 48. The monitor 47 can display a graphical user interface for the user. In addition to the monitor 47, computers typically include other peripheral output devices (not shown), such as speakers and printers.

The computer 20 may operate in a networked environment using logical connections to one or more remote computers or servers, such as remote computer 49. These logical connections are achieved by a communication device coupled to or a part of the computer 20; the invention is not limited to a particular type of communications device. The remote computer 49 can be another computer, a server, a router, a network PC, a client, a peer device or other common network node, and typically includes many or all of the elements described above I/O relative to the computer 20, although only a memory storage device 50 has been illustrated. The logical connections depicted in FIG. 5 include a local area network (LAN) 51 and/or a wide area network (WAN) 52. Such networking environments are commonplace in office networks, enterprise-wide computer networks, intranets and the internet, which are all types of networks.

When used in a LAN-networking environment, the computer 20 is connected to the LAN 51 through a network interface or adapter 53, which is one type of communications device. In some embodiments, when used in a WAN-networking environment, the computer 20 typically includes a modem 54 (another type of communications device) or any other type of communications device, e.g., a wireless transceiver, for establishing communications over the wide-area network 52, such as the internet. The modem 54, which may be internal or external, is connected to the system bus 23 via the serial port interface 46. In a networked environment, program modules depicted relative to the computer 20 can be stored in the remote memory storage device 50 of remote computer, or server 49. It is appreciated that the network connections shown are exemplary and other means of, and communications devices for, establishing a communications link between the computers may be used including hybrid fiber-coax connections, T1-T3 lines, DSL's, OC-3 and/or OC-12, TCP/IP, microwave, wireless application protocol, and any other electronic media through any suitable switches, routers, outlets and power lines, as the same are known and understood by one of ordinary skill in the art.

Thus, an example system, method and machine readable medium for visualizing and navigating knowledge domains have been described. Although specific example embodiments have been described, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. A non-transitory computer readable storage device comprising instructions that when executed by a processor execute a process comprising:
    storing visual content in a computer storage device;
    displaying the visual content on a display unit in an undistorted, overview projection;
    receiving input from a user to focus on a topic in the undistorted, overview projection;
    transforming the undistorted, overview projection into a focused display showing the topic selected by the user and content related to the topic selected by the user in a continuous sequence of increasingly distorted projections;
    determining a relation among displayed topics;
    fading out topics that are not related to the topic selected by the user during the transforming from the undistorted, overview projection to the focused display; and
    moving content that is related to the topic selected by the user towards the selected topic on the focused display such that at a commencement of the transforming, movement of the content that is related to the topic selected by the user obeys a cambering hyperboloid projection, and in a course of the transforming, paths of the content that is related to the topic selected by the user are increasingly decoupled from the projected plane;
    wherein content that is unrelated to the topic selected by the user becomes invisible at the end of the transformation irrespective of a location of the unrelated content on the undistorted, overview projection;
    wherein content that is related to the topic selected by the user moves towards the topic selected by the user on the focused display; and
    wherein the decoupling from the projected plane comprises a changing of a size of content that is related to the topic selected by the user and a distance of content that is related to the topic selected by the user from the selected topic as follows:
    calculating a projected distance as follows:

$$r(d) = r_\infty \left(1 - \frac{1}{fd+1}\right)$$

wherein, the convergence radius $r_\infty$ is calculated from $r_h$, h and f as follows:

$$r_\infty = \frac{r_h}{1 - \frac{1}{fh+1}}$$

wherein a scale factor at a point with a logical distance d from the center of the focused display is calculated as a ratio r(d)d as follows:

$$\frac{r(d)}{d} = \frac{r_h}{h}\left(\frac{fh+1}{fd+1}\right)$$

wherein
    f comprises a factor indicating a degree of a fisheye distortion;
    d comprises the logical distance of content to the center of the focused display;
    r comprises a projected distance of content to the center of the focused display;
    h comprises a logical horizon comprising a logical distance between the center of the focused display and a center of content at a border of the focused display; and
    $r_h$ comprises a projected horizon comprising a number of pixels from a center of the focused display to the border of the focused display.

2. The computer readable medium of claim 1, comprising calculating an adjusted logical distance of the projected distance as follows:

$$d' = \frac{d_{target} - d}{f_1 - f_0}(f - f_0) + d$$

wherein
    d' comprises the adjusted logical distance;
    $d_{target}$ comprises the adjusted logical distance at a completion of the transforming;
    $f_1$ comprises a fisheye factor at the completion of the transforming;
    $f_0$ comprises the fisheye factor at a start of the transforming; and
    f comprises the fisheye factor at a current transforming step.

* * * * *